United States Patent [19]
Di Cesare et al.

[11] Patent Number: 5,942,442
[45] Date of Patent: Aug. 24, 1999

[54] DETECTION OF LOW LEVEL ANALYTES IN SAMPLES USING AGGLUTINATION REACTION CAPILLARY SLIDE TEST AND APPARATUS THEREFOR

[75] Inventors: Joseph L. Di Cesare, Redding, Conn.; Steven M. Rosen, Mountain Lakes, N.J.

[73] Assignees: The Perkin-Elmer Corporation, Norwalk, Conn.; Roche Dianostic Systems, Inc., Branchburg, N.J.

[21] Appl. No.: 08/831,206

[22] Filed: Apr. 2, 1997

[51] Int. Cl.$^6$ ............... G01N 33/543; G01N 33/546; G01N 33/547
[52] U.S. Cl. .......... 436/501; 436/178; 436/518; 436/533; 436/534; 436/535; 436/807; 436/815; 436/822; 436/824
[58] Field of Search .................. 436/178, 518, 436/533, 534, 535, 807, 815, 822, 824, 501

[56] References Cited

U.S. PATENT DOCUMENTS

| | | | |
|---|---|---|---|
| 4,596,695 | 6/1986 | Cottingham | 422/58 |
| 4,597,944 | 7/1986 | Cottingham | 422/73 |
| 4,775,515 | 10/1988 | Cottingham | 422/73 |
| 5,019,351 | 5/1991 | Schulz | 422/99 |
| 5,236,826 | 8/1993 | Marshall | 435/7.92 |
| 5,501,949 | 3/1996 | Marshall | 435/5 |
| 5,552,325 | 9/1996 | Nochumson et al. | 436/178 |

FOREIGN PATENT DOCUMENTS 471570  2/1992  European Pat. Off. ........ A61B 10/00

OTHER PUBLICATIONS

"Screening for Drugs of Abuse with the Roche ONTRAK Assays", Journal of Analytical Toxicology, vol. 16, May/Jun. 1992.

"3M Empore™, Strontium Rad Disks", IBC Advanced Technologies, Inc., 1995.

"Protrans™ Affinity Disks", ICN Biomedicals, Inc.

*Primary Examiner*—David Saunders
*Attorney, Agent, or Firm*—Ohlandt, Greeley, Ruggiero & Perle, L.L.P.; George W. Rauchfuss, Jr.

[57] ABSTRACT

Apparatus and method for detection of low levels of about 1 ppb of analyte in samples using an enclosed permeable membrane enrichment device and agglutination reaction slide test apparatus.

28 Claims, 2 Drawing Sheets

DETECTION OF LOW LEVEL ANALYTES IN SAMPLES USING AGGLUTINATION REACTION CAPILLARY SLIDE TEST AND APPARATUS THEREFOR

FIELD OF THE INVENTION

This invention relates to apparatus and procedure for the detection of low levels, 10 ppb and more particularly 1 ppb or less, of analytes possibly present in samples using agglutination reaction capillary slide test apparatus.

BACKGROUND OF THE INVENTION

Improved test apparatus has been provided for detection of substance for agglutination reactions. As examples of such improved test apparatus there can be mentioned U.S. Pat. Nos. 4,596,695; 4,597,944 and 4,775,515 of Hugh V. Cottingham and the agglutination slide device disclosed in U.S. Pat. No. 5,019,351 of Peter Schulz.

The agglutination test is based on latex agglutination-inhibition principles in which there is competition for binding to an antibody between the analyte and latex particles coated with an analyte analog or conjugate of the analyte. A sample is placed in the mixing well of a slide apparatus of the type disclosed in the aforementioned U.S. Pat. No. 5,019,351 along with the latex particles coated with the analyte analog or conjugate and the antibody. The mixture traverses the capillary path of the slide apparatus by capillary action to a viewing area. If there is no analyte in the sample, the latex particles with the analyte analog or conjugate form large clumps of particles (agglutinates) by binding to the antibody. However, when analyte is present in the sample, the analyte competes with the labeled latex particles for reaction with the antibody and the analyte preferentially binds to the antibody and inhibits or prevents reaction of the antibody with the labeled latex particles and thereby inhibits or prevents agglutination of the latex particles. Thus, the presence of agglutination of the latex particles is evidence of the absence of the analyte from the sample, whereas the absence of significant agglutination of the latex particles is evidence of the presence of the analyte in the sample, when the presence or absence of agglutination of the latex particles is visually observed in the viewing area of the slide apparatus.

Using the aforementioned technology and the agglutination slide apparatus disclosed in the aforesaid patents, test kits have been marketed for the easy, rapid determination of various biological substances such as hormones, tumor markers and the like and also for drugs of abuse, such as amphetamines, barbituates, cocaine, marijuana, morphines, phencyclidine and the like from biological samples, such as urine, blood or other body fluids. Such test apparatus and assay procedure have permitted easy and rapid field assays of biological fluids for such biological substances and drugs of abuse. Such rapid assays are able to be readily conducted in the field and require no instrumentation for analysis of the results. A visual qualitative result is observable in the slide viewing area, generally within about three to five minutes or less from the time of mixing the sample, labeled latex particles and antibody in the mixing well of the slide apparatus.

The use of such agglutination reaction slide apparatus has been highly beneficial, permitting on-site field analysis, that is, in a non-laboratory setting, by a simple, easy procedure without requiring other instrumentation. An example of such an assay test system for drugs of abuse is the ONTRAK test system sold by Roche Diagnostic Systems, Inc. of Somerville, N.J. Thus, this technology has replaced, at least in part, screening assay procedures previously required to be used, such as thin layer chromatography or liquid chromatography, enzyme immunoassay, fluorescence polarization immunoassay or radioimmuno-assay, requiring some type of instrumentation.

However, such agglutination reaction slide assay technology has been found to have an especially limiting drawback, namely that the concentration of analyte in the sample being analyzed must be at a relatively high concentration level of at least about 50 ppb or more in order to produce agglutination-inhibition to provide the desired visual result since generally only about a 11 $\mu$l sample volume in a total reaction volume of about 160 $\mu$l is able to be put into the mixing well of a slide apparatus. This drawback has prevented such agglutination slide reaction assay technology from being usable to detect analytes such as pesticides or environmental toxins in environmental samples, such as water, effluent water, soil, sludge, manure wastes or sediments or the like, where the pesticide residues or environmental toxins are or may be present only in very low concentration, such as about 1 ppb or less.

Similarly, because of the generally low levels of LSD, i.e. lysergic acid diethylamide, in biological samples, e.g. below about 1.5 ppb in urine, it has not been possible to utilize the ONTRAK test system for detecting this common drug of abuse.

It has also previously been proposed to detect analytes by use of affinity chromatography techniques where an affinity membrane with a functional group and antibody attached directly to the membrane was permitted to come into intimate contact with the sample suspected of containing the analyte of interest. However, there is insufficient binding capacity for a number of reasons, including low surface binding area and loss of functionality of the antibody, and therefore generally only about 20% to about 40% of analyte is able to be recovered for detection and assay. Thus, such affinity chromatography techniques have also not provided a satisfactory field assay procedure for detection of 10 ppb or 1 ppb levels of pesticides and environmental toxins in environmental samples.

It is therefore highly desirable that an agglutination slide reaction assay system be available for quick, easy, in-the-field assays samples containing low level of analytes such as pesticides or environmental toxins in environmental samples and low levels LSD or other drugs of abuse in biological samples.

SUMMARY OF THE INVENTION

The invention provides an improved agglutination reaction slide assay system and procedure for detection of low level analytes in samples, particularly in environmental or biological samples and a device for use in such system and procedure.

With the present invention, the agglutination reaction slide apparatus of the type disclosed in the aforementioned patents can now be employed to detect analytes present in samples at levels below 10 ppb, even below 1 ppb or less. This is accomplished by means of a novel sample enrichment procedure utilizing a novel sample enrichment device along with agglutination-inhibition assay procedures in an agglutination reaction slide apparatus of the type disclosed in the aforementioned U.S. Pat. No. 5,019,351, the disclosure of which is incorporated herein by reference thereto.

In accordance with the invention there is provided a method for detecting the presence of an analyte in a sample, particularly in an environmental or biological sample, in an amount of 10 ppb or less, especially in an amount of 1 ppb or less, wherein said method comprises:

(1) providing a determinable volume of the sample;

(2) providing a permeable membrane in a liquid tight housing, the housing having an inlet port to a first surface of the membrane and an outlet port from a second, opposite surface of the membrane, said permeable membrane having pores or interstices therein and having latex particles, coated with an antibody or affinity reagent to the analyte, located on the first surface and entrapped in the pores or interstices of the permeable membrane;

(3) introducing the determinable volume of said sample, under a pressure differential, into the inlet port for travel through the permeable membrane and out the outlet port, with analyte in the sample binding to the antibody or affinity reagent coated on the particles;

(4) thereafter, employing a volume of eluting solvent which is a fractional part of said determinable volume of sample, eluting analyte from the coated particles out the outlet port into a container as a concentrated analyte solution having a concentr ation of the analyte of at least about 50 ppb;

(5) introducing into and mixing in a receiving well of an agglutination reaction slide assay device (a) said concentrated analyte solution, (b) particles coated with an analyte analog or conjugate thereof, and (c) antibody to the analyte, introducing this m ixture from the receiving well into a capillary track region of the slide assay device and permitting the mixture to traverse the capillary track region to a viewing region of the slide assay device; and (6) visually determining the absence or presence of analyte in the determinable volume of sample by observing the pr esence or absence, respectively, of significant agglutinate d particles in th e viewing region of the slide assay device.

In a more particular aspect of this invention there is provided a method for detect ing the presence of an analyte present in an environmental sample in an amount of 1 ppb or less, said method comprising:

(1) providing a determinable volume of said environmental sample;

(2) providing a permeable membrane in a liquid tight housing, said housing having an inlet port to a first surface of the membrane and an outlet port from a second, opposite surface of the membrane, said permeable membrane having pores or interstices therein and having latex particles coated with an antibody or affinity reagent to the analyte, located on the first surface and entrapped in the pores or interstices of the permeable membrane;

(3) introducing said determinable volume of environmental sample under a pressure differential into the inlet port for travel through the permeable membrane and out the outlet port, with analyte in the sample binding to the phase, antibody or affinity reagent coated on the particles;

(4) thereafter, employing a volume of eluting solvent which is a fractional part of the determinable volume of environmental sample, eluting analyte from the coated particles out the outlet port into a container as a concentrated analyte solution having a concentration of the analyte of at least about 50 ppb;

(5) introducing into and mixing in a receiving well of an agglutination reaction slide assay device (a) said concentrated analyte solution, (b) latex particles coated with a n analyte analog or conjugate thereof, and (c) antibody to the analyte, introducing this mixture from the receiving well into a capillary track region of the slide assay device and permitting the mixture to traverse the capillary track region to a viewing region of the slide assay device; and (6) visually determining the absence or presence of the analyte in the determinable volume of environmental sample by observing the presence or absence, respectively, of significant agglutinated latex particles in the viewing region of the slide assay device.

BRIEF DESCRIPTION OF THE DRAWINGS

The invention will be described in detail in the following illustrative embodiment with reference to the drawings, in which.

DETAILED DESCRIPTION OF THE INVENTION

Figure 1:
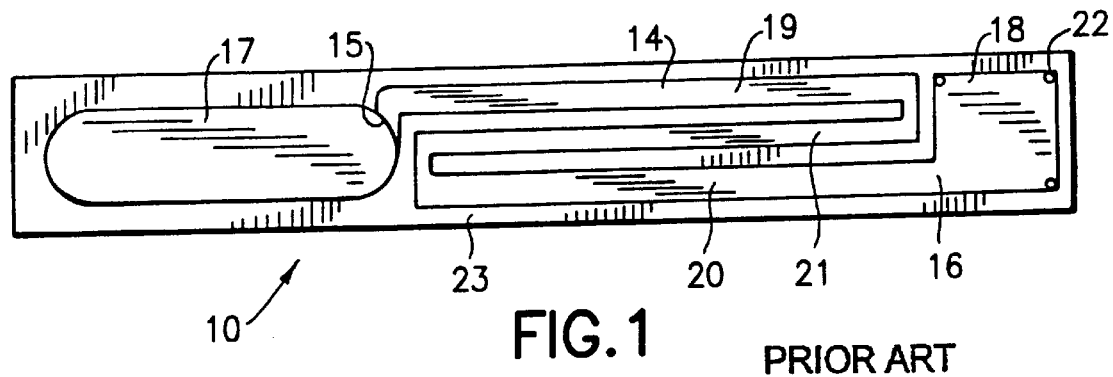
FIG. 1 is a plan view of an agglutination reaction slide assay device for agglutination tests of samples according to this invention.

This invention provides a ready and reliable field agglutination reaction assay for detection of analytes, particularly organic analytes such as pesticides, polyaromatic organic compounds, organic toxins and microorganisms such as bacteria, that are present in environmental samples at very low concentrations of about 1 ppb or less. This invention enables a field assay to be conducted in less than about 10 minutes to determine if an environmental sample contains the low level analyte being assayed.

Although the assay procedure of this invention is particularly useful for such detection of low level analytes in environmental samples, it has also been discovered that in various aspects thereof the invention procedure and apparatus is also particularly useful for slide agglutination reaction assay for drugs of abuse in biological samples, such as, for example LSD, that have heretofore not been suitably assayable by the slide agglutination reaction procedure because of the presence of the analyte in biological samples at levels considerably below the 50 ppb level considered necessary for a successful agglutination reaction assay. The procedure of this invention makes it possible to assay for LSD or other low level drugs of abuse in biological samples by the agglutination reaction slide assay procedure.

The assay procedure of this invention is especially suitable for use in assaying any type of field environmental sample, such as, for example, water, effluent water, soil, sludge, wastes or sediments and the like, where the analyte may be present in amounts of about 1 ppb or less. The assay procedure can be employed to assay for any suitable analyte in the environmental sample. Of particular interest are pesticides, polyaromatic carcinogenic materials, organic toxins and microorganisms such as bacterial contaminants. For example, the improved assay procedure of this invention can be employed to assay for pesticides such as atrazine, aldrin, α-BHC, β-BHC, γ-BHC, δ-BHC, 4,4'-DDD, 4,4'-DDE, 4,4'-DDT, dieldrin, endosulfan I, endosulfan II, endosulfan sulfate, endrin, endrin aldehyde, endrin ketone, heptachlor, heptachlor epoxide, methoxychlor and the like, polyaromatic carcinogen materials such as polychlorinated biphenyls, polychlorinated polyphenyls and PCP and microorganisms such as *E. coli* organisms, Salmonella organisms and the like.

In addition the assay procedure of this invention is also suitable for use in assaying a biological sample, such as urine, blood, plasma, or other body fluids, for analytes, such as LSD, that may be present in the biological sample in levels substantially below the 50 ppb currently needed for a slide agglutination reaction assay.

The agglutination reaction assay can be conducted on a suitable agglutination reaction slide assay device known in the art, such as that disclosed in the aforementioned U.S. Pat. No. 5,019,351 and illustrated in FIG. 1. The assay test element is represented by the general reference numeral 10. The test element comprises a receiving and mixing well 17 where a sample to be analyzed for analyte and appropriate reagents including antibody to the analyte and particles coated with an analyte analog or conjugate are mixed. The mixture is then permitted to enter a serpentine-shaped capillary reaction track 14 through upstream capillary entrance 15. The mixture proceeds along track 14 through upstream capillary region 19, intermediate capillary region 21 and downstream capillary region 20, exiting the capillary track by downstream capillary exit 16, entering a viewing or observation region in the form of viewing well 18. Viewing region 18 can be provided with bores 22 for venting the viewing region. A wall 23 extends around receiving area 17, viewing area 18 and capillary track region 14 to provide a fluid-tight bonding around these regions.

Figure 2:
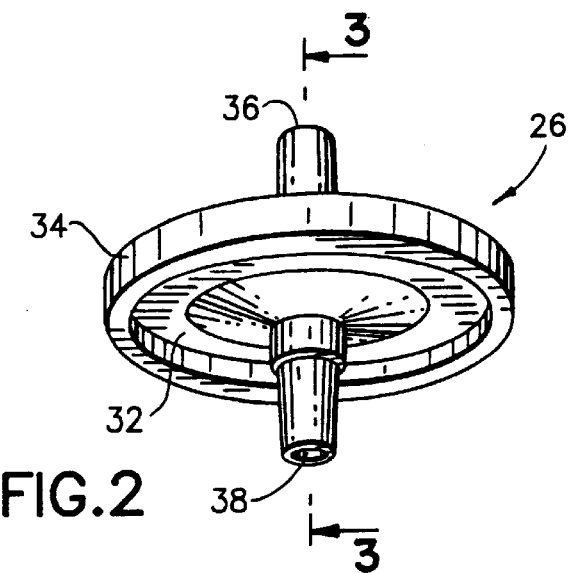
FIG. 2 is a perspective view of a permeable membrane in a fluid tight housing for use in this invention.
Figure 3:
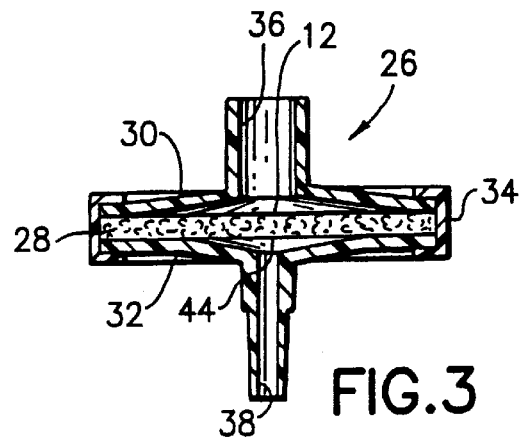
FIG. 3 is a cross-sectional view along line 3—3 of FIG. 2.
Figure 4:
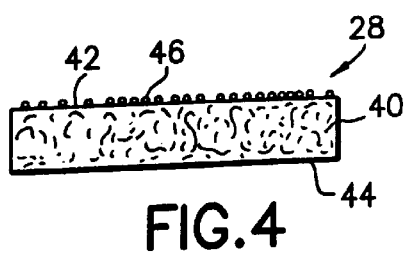
FIG. 4 is an enlarged cross-sectional view of a membrane element of FIG. 3.

Before an environmental or biological sample containing less than about 10 ppb, especially less than about 1 ppb of suspected analyte can be assayed in the reaction slide device of FIG. 1, the sample must be enriched or concentrated. Shown in FIGS. 2, 3 and 4 is an element for such a sample enrichment device, indicated generally by reference numeral 26. The element 26 comprises a suitable porous or permeable membrane 28 housed in the enrichment element and held between an inlet cap 30 and an outlet cap 32 by a retainer housing 34. Inlet cap 30 is provided with a generally centrally located inlet port 36 and outlet cap 32 is provided with a generally centrally located outlet port 38. Retainer housing 34 provides a fluid-tight housing around the inlet cap 30, permeable membrane 28 and outlet cap 32. The permeable membrane 28 is shown in greater detail in FIG. 4.

The membrane 28 is a disc 40 made of a permeable solid phase material which itself is inert to the analyte to be analyzed. The membrane disc 40 has a top surface 42 and a bottom surface 44 with holes or interstices therethrough. Particles 46, coated with an antibody or an affinity reagent to the analyte, are entrapped in the pores and interstices and located on the top surface 42 of the membrane disc 40.

The pores or interstices of the membrane disc 40 will be slightly smaller in size or diameter than the diameter of the coated particles 46. For example, the particles may generally have a diameter of from about 0.6 to 1.0 μm, preferably from about 0.8 to 1.0 μm, and the pores or interstices will generally be in the range of from about 0.4 to about 0.7 μm, preferably from about 0.4 to 0.5 μm. The disc can be composed of any suitable substance inert to the reactants, such as, for example, paper, glass fiber, cotton, cellulose, cellulose acetate and synthetic polymeric material such as polytetrafluoroethylene, polyethylene, polypropylene, polyvinylidene fluoride and the like. A preferred membrane disc will be about 25 mm in diameter and have a capacity of at least 1 μg analyte, most preferably a glass fiber membrane disc of said size. The particles can be made of a wide variety of suitable materials, such as, for example, silica or glass, cellulose and synthetic polymers. A preferred form of the particles is a latex of polystyrene beads.

Figure 5:
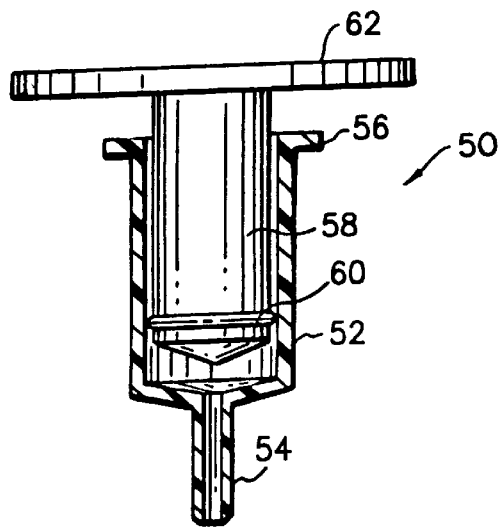
FIG. 5 is a partial cross-sectional view of a pressure differential providing device for use in the assay procedure of this invention.

The particles are first bound to an antibody or affinity reagent for the analyte in a generally know manner, either covalently or non-covalently. The selection of the particular material to be coated to the particles will be driven by the analyte to be assayed. One will select a suitable material which has selective affinity for the analyte, such as an antibody or an affinity reagent for the analyte. Then an aspiration/expulsion device, such as a manually operated syringe 50 (FIG. 5) is employed to entrap the coated particles in the pores or interstices and also to place said coated particles on the top surface of the membrane disc 40.

The syringe 50 comprises a tubular housing 52 having at one end a centrally located conduit 54 for aspiration of material into and expiration of material from the housing. At the opposite end the tubular housing terminates in a shoulder 56. Located within housing 52 is a movable tubular piston 58 held in fluid tight relationship to the interior of tubular housing 52 by a sealing means 60, such as an O-ring. External of housing 52 piston 58 is provided with a suitable handle 62 for manual aspiration and expiration of material.

Figure 6:
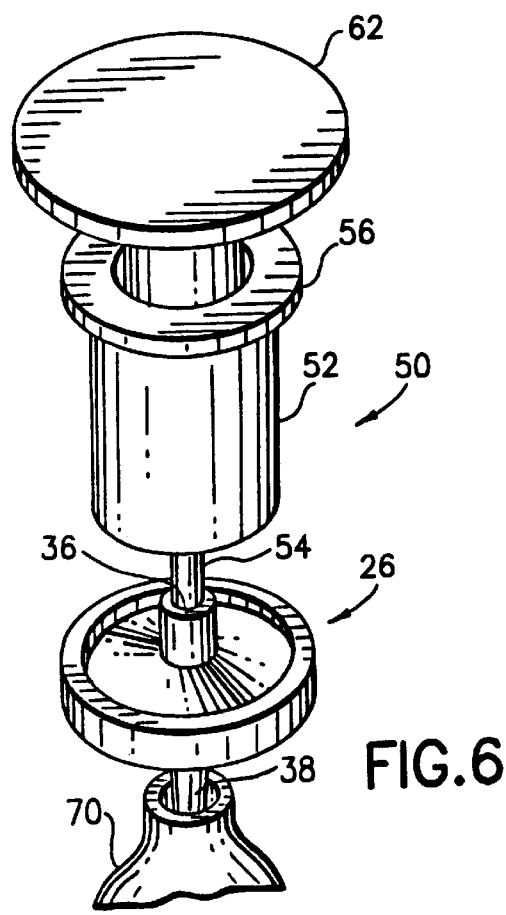
FIG. 6 is a partial cross-sectional view of apparatus for preparing a concentrated analyte solution for use in the assay procedure of this invention.

Antibody or affinity reagent coated particles 46 in a suitable fluid medium are aspirated into housing 52 of syringe 50 through conduit 54, then the conduit is placed in inlet port 36 (FIG. 6) of the enrichment device 26 and the coated particles are expelled from the syringe into the enrichment device entrapping the coated particles in the pores or interstices of the disc 40 and the top surface 42 thereof with the fluid medium passing through disc 40 and out outlet port 38 into a suitable collection container 70. The syringe is then removed from inlet port 36.

The membrane disc 40 with the coated particles located in the pores and interstices thereof and on the top surface of the disc is able to bind substantially all the analyte in the sample being processed through the enrichment device leading to at least about 88% or more, generally about 95 to 100% recovery of the analyte, compared to the about 10 to 40% recovery of analyte usually obtained with antibody or affinity reagent bound directly to the membranes.

Thereafter, a sample containing less than about 10 ppb, preferably less than about 1 ppb of analyte, is aspirated into a similar syringe 50, the syringe similarly attached to inlet port 36 and the environmental sample is expelled into enrichment device 26. Analyte in the sample binds to the antibody or affinity reagent coated particles which are on the top surface of the disc 40 and entrapped in the pores and interstices of the membrane disc while the fluid in the sample permeates the disc and flows out the outlet port 38 into a suitable collection vessel or container 70.

The analyte bound to the coated particles on and in the membrane disc 40 is then eluted with a small amount of elution solvent from a similar syringe 50 or squeezable container introduced into inlet pore 36 of enrichment device 28 to unbind analyte from the coated particles and elute the freed analyte out outlet port 38 into a suitable collection vessel or container 70. The elution solvent must be one that is compatible with and does not interfere with the agglutination reaction occurring in the slide apparatus, possess sufficient viscosity, similar to water, to permit movement of the reaction mixture in the slide apparatus and have no deleterious effects on antibody binding to analyte in the agglutination reaction slide. As examples of such suitable eluting solvents, there may be mentioned, for example, methanol or a solution of methanol, ethylene glycol, polyvinylpyrrolidone and sodium chloride, especially a solvent solution of about 60% methanol (v/v), about 40% ethylene glycol (v/v), about 4% polyvinyl pyrrolidone (w/v) and about 2% NaCl (w/v).

The small amount of elution solvent employed is a small, fractional volume part compared to the volume of sample introduced into the enrichment device. For example, use of a 50 ml sample containing the analyte at a concentration of 1 ppb and use of 1 ml of elution solvent enables one to obtain about a 50-fold concentration factor so that the eluted 1 ml sample contains analyte at a concentration of about 50 ppb.

After the sample has been suitably enriched or concentrated in the foregoing manner, generally about 11 $\mu$l of the concentrated analyte solution is introduced into the receiving/mixing well 17 of slide apparatus 10 along with particles coated with an analyte analog or conjugate thereof and antibody to the analyte and any necessary reaction buffers. This mixture is introduced to the capillary track region 14 through upstream inlet 15 and permitted to traverse the serpentine capillary track 19, 21, 20 to downstream exit 16 and into viewing region 18. If no analyte was present in the environmental sample, and thus in the enriched solution thereof, the antibody will react with the analyte analog or conjugate in the capillary track causing agglutination of the particles. However, if analyte was present in the environmental sample, and thus in the enriched solution thereof, the analyte will bind to its antibody and prevent or inhibit the antibody from reacting with the analog or conjugate of the coated latex particles thus preventing or inhibiting particle agglutination.

Observation of the viewing area, after traverse of the sample and reagents through the capillary track, will enable a result to be visually determined: positive for analyte=no agglutination; negative for analyte=agglutination.

The assay procedure as just described is a relatively simple procedure requiring no special instrumentation and thus is readily conducive to quick field assays, i.e. assays in a non-laboratory environment, such as in nature, or offices or homes and the like. Generally, the whole assay procedure including both the enrichment steps and the agglutinate reaction test can be conducted in about 10 minutes or less, generally about 5 minutes or less for the sample enrichment phase and 5 minutes or less for the agglutination reaction test phase.

Moreover, all the materials and devices needed for the assay procedure are easily produced, inexpensive and can be readily disposed of in an environmental acceptable manner.

It is to be appreciated that the coated latex particles 46 will be coated with the appropriate antibody or affinity reagent for the specific analyte to be assayed. The relative size of the particles 46, the pores and interstices of the membrane disc 40 will be such that the particles are trapped in the pore or interstices and retained on the top surface of the disc and not pass through the disc.

All that is required to do a field assay for an analyte present in an environmental sample at a level of 10 ppb or less, particularly 1 ppb or less, is an enrichment device with a membrane having appropriately coated particles entrapped therein, one or more syringes and collection containers, the agglutination reaction slide device and the appropriate reagents, such as eluting solvent, latex particles having an analyte or conjugate bound thereto, antibody for the analyte and any reaction buffer required or considered necessary.

The invention is further exemplified by the following illustrative examples of assays for the pesticide atrazine and for LSD.

EXAMPLE 1

Antibody for atrazine, polyclonal antiserum from rabbit, was used to coat 0.8 $\mu$m polystyrene latex particles. The antibodies were enriched by ammonium sulfate precipitation by slowly adding an equal volume of saturated (100%) ammonium sulfate to the antiserum in an ice bath to precipitate the antibodies. The precipitated antibodies were resuspended in a phosphate buffer saline solution (PBS) at about pH 7.0±0.1 and centrifuged to provide a concentration of antibodies of about 17 mg/ml.

Commercially available white polystyrene latex particles of 0.8 $\mu$m in a 30% stock solution was washed four times with 50 mM methyl ethane sulfonic acid (MES) buffer solution at pH 6.0±0.1 at about 4° C. to remove the storage buffer.

The purified antibody was diluted with 50 mM MES buffer and equal volume of the serial diluted antibody solution was mixed with the washed latex particles and stirred overnight to sensitize the washed latex particles. Unbound sights on the latex microparticles were blocked by adding an equal volume of 100 mg/ml bovine serum albumin (BSA) in MES buffer to the antibody-latex microparticles mixture. After about an hour of blocking, the latex-antibody-BSA mixture was washed and resuspended in 50 mM MES buffer and the final latex solution was adjusted to 10% solids.

Employing a syringe, 0.6 ml of the 100% solid latex particles-antibody-BSA mixture is aspirated into the syringe and expelled therefrom at a flow rate of 0.5 ml/min. through a glass fiber membrane disc, having 0.45 $\mu$m pores or interstices, in an enrichment device as illustrated in FIG. 2, to trap the bound latex particles in the pores and interstices and on the top surface of the membrane disc. Thereafter, using a syringe, about 50 ml of an environmental solution known to contain about 1 ppb atrazine is passed from the syringe chamber through the membrane disc at a flow rate of 3 ml/min. to bind atrazine in the analyte sample to the antibody coated latex particles in and on the membrane disc.

After passage of the 50 ml of atrazine solution through the membrane disc of the enrichment device, bound analyte is eluted from the latex particles with 1 ml of 100% HPLC grade methanol at a flow rate of about 1 ml/min., and the eluent collected in a suitable collection container. The eluent collected is about a 50 fold concentrated solution of atrazine.

Assay of such an enriched analyte solution is conducted according to this invention by placing about 11 $\mu$l of the concentrated atrazine analyte solution, about 50 $\mu$l atrazine-BSA conjugated latex particles, about 50 $\mu$l antibody to atrazine, and about 50 $\mu$l buffer in the receiving and mixing well of an agglutination reaction slide apparatus of the type illustrated in FIG. 1, mixing the reagents in said well, introducing the mixture into the capillary track and permitting the reacting mixture to flow into the viewing area of the slide. Absence of agglutinated latex particles in the viewing confirms the presence of atrazine in the environmental water solution. In contradistinction, if the environmental water sample containing 1 ppb atrazine had been subjected to the same agglutination reaction assay without the enrichment procedure, the assay would have resulted in agglutination of the latex particles in the slide, falsely indicating the absence of atrazine in the environmental water solution.

EXAMPLE 2

Antibody for LSD, polyclonal antiserum from goat, was used to coat 0.8 μm polystyrene latex particles. The antibodies were enriched by ammonium sulfate precipitation by slowly adding an equal volume of saturated (100%) ammonium sulfate to the antiserum in an ice bath to precipitate the antibodies. The precipitated antibodies were resuspended in a phosphate buffer saline solution (PBS) at about pH 7.0±0.1 and centrifuged to provide a concentration of antibodies of about 28 mg/ml.

Commercially available white polystyrene latex particles of 0.8 μm in a 30% stock solution was washed four times with 50 mM methyl ethane sulfonic acid (MES) buffer solution at pH 6.0±0.1 at about 4° C. to remove the storage buffer.

The purified antibody was diluted with 50 mM MES buffer and equal volumes of the serial diluted antibody solution was mixed with the washed latex particles and stirred overnight to sensitize the washed latex particles. Unbound sights on the latex microparticles were blocked by adding an equal volume of 100 mg/ml bovine serum albumin (BSA) in MES buffer to the antibody-latex microparticles mixture. After about an hour of blocking, the latex-antibody-BSA mixture was washed and resuspended in 50 mM MES buffer and the final latex solution was adjusted to 10% solids.

Employing a syringe, 0.6 ml of the 100% solid latex particles-antibody-BSA mixture is aspirated into the syringe and expelled therefrom at a flow rate of about 0.5 ml/min. through a glass fiber membrane disc, having 0.45 μm pores or interstices, in an enrichment device as illustrated in FIG. 2, to trap the bound latex particles in the pores and interstices and on the top surface of the membrane disc. Thereafter, using a syringe, about 50 ml of a urine sample known to contain about 1 ppb LSD is passed from the syringe chamber through the membrane disc at a flow rate of 3 ml/min. to bind LSD in the analyte sample to the antibody coated latex particles in and on the membrane disc.

After passage of the 50 ml of analyte solution through the membrane disc of the enrichment device, bound LSD is eluted from the latex particles with 1 ml of 100% HPLC grade methanol at a flow rate of about 1 ml/min., and the eluent collected in a suitable collection container. The eluent collected is about a 50 fold concentrated solution of LSD.

Assay of the analyte solution is conducted by placing about 11 μl of the concentrated LSD analyte solution, about 50 μl LSD-BSA conjugated latex particles, about 50 μl antibody to LSD, and about 50 μl buffer in the receiving and mixing well of an agglutination reaction slide apparatus of the type illustrated in FIG. 1, mixing the reagents in said well, introducing the mixture into the capillary track and permitting the reacting mixture to flow into the viewing area of the slide. Absence of agglutinated latex particles in the viewing confirms the presence of LSD in the original urine sample. In contradistinction, if the urine sample containing 1 ppb LSD had been subjected to the same agglutination reaction assay without the enrichment procedure, the assay would have resulted in agglutination of the latex particles in the slide, falsely indicating the absence of LSD in the environmental water solution.

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. A method for detecting the possible presence of an analyte in a sample in an amount of 10 ppb or less, said method comprising:

(1) providing a determinable volume of said sample;
   (2) providing a permeable membrane in a liquid tight housing, said housing having an inlet port to a first surface of the membrane and an outlet port from a second, opposite surface of the membrane, said permeable membrane having pores or interstices therein and having latex particles coated with an antibody or affinity reagent to the analyte, located on the first surface and entrapped in the pores or interstices of the permeable membrane;
   (3) introducing said determinable volume of sample under a pressure differential into the inlet port for travel through the permeable membrane and out the outlet port, with analyte in the sample binding to the antibody or affinity reagent coated on the particles;
   (4) thereafter, employing a volume of eluting solvent which is a fractional part of the said determinable volume of sample, said eluting solvent comprising a solution of methanol, ethylene glycol, polyvinyl pyrrolidone and NaCl, eluting analyte from the coated particles out the outlet port into a container as a concentrated analyte solution having a concentration of the analyte of at least about 50 ppb;
   (5) introducing into and mixing in a receiving well of an agglutination reaction slide assay device (a) said concentrated analyte solution, (b) particles coated with an analyte analog or conjugate thereof, and (c) antibody to the analyte to form a mixture, introducing this mixture from the receiving well into a capillary track region of the slide assay device and permitting the mixture to traverse the capillary track region to a viewing region of the slide assay device; and
   (6) visually determining the absence or presence of the analyte in the determinable volume of sample by observing the presence or absence, respectively, of significant agglutinated latex particles in the viewing region of the slide assay device.

2. A method according to claim 1 wherein the pores and interstices of the permeable membrane are within the range of from about 0.4 to 0.7 μm and the coated particles located on the first surface and entrapped in the pores and interstices of the permeable membrane are within the range of about 0.8 to 1.0 μm.

3. A method according to claim 2 wherein the permeable membrane is a glass fiber membrane.

4. A method according to claim 2 wherein the coated particles are polystyrene latex particles.

5. A method according to claim 1 wherein the sample is an environmental sample and the analyte is an organic pesticide.

6. A method according to claim 5 wherein the analyte is atrazine.

7. A method according to claim 1 wherein the sample is a biological sample and the analyte is LSD.

8. A method according to claim 1 wherein the sample is an environmental sample, the analyte is atrazine, the coated particles are polystyrene latex particles within the range of about 0.8 to 1.0 µm, the permeable membrane is a glass fiber membrane having pores and interstices in the range of from about 0.4 to 0.7 µm and the fractional volume of the eluting solvent is no greater than about 1/50 of the determinable volume of sample.

9. A method according to claim 1 wherein the eluting solvent is a solution of about 60% methanol (v/v), about 40% ethylene glycol (v/v), about 4% polyvinyl pyrrolidone (w/v) and about 2% NaCl (w/v).

10. A method according to claim 8 wherein the eluting solvent is a solution of about 60% methanol (v/v), about 40% ethylene glycol (v/v), about 4% polyvinyl pyrrolidone (w/v) and about 2% NaCl (w/v).

11. A method for detecting the possible presence of an analyte in an environmental sample in an amount of 1 ppb or less, said method comprising:

(1) providing at determinable volume of said environmental sample;

(2) providing a permeable membrane in a liquid tight housing, said housing having an inlet port to a first surface of the membrane and an outlet port from a second, opposite surface of the membrane, said permeable membrane having pores or interstices therein and having latex particles, coated with an antibody or affinity reagent to the analyte, located on the first surface and entrapped in the pores or interstices of the permeable membrane;

(3) introducing said determinable volume of environmental sample under a pressure differential into the inlet port for travel through the permeable membrane and out the outlet port, with analyte in the sample binding to the antibody or affinity reagent coated on the particles;

(4) thereafter, employing a volume of eluting solvent which is a fractional part of the determinable volume of environmental sample, said eluting solvent comprising a solution of methanol, ethylene glycol, polyvinyl pyrrolidone and NaCl, eluting analyte from the coated particles out the outlet port into a container as a concentrated analyte solution having a concentration of the analyte of at least about 50 ppb;

(5) introducing into and mixing in a receiving well of an agglutination reaction slide assay device (a) said concentrated analyte solution, (b) latex particles coated with an analyte analog or conjugate thereof, and (c) antibody to the analyte to form a mixture, introducing this mixture from the receiving well into a capillary track region of the slide assay device and permitting the mixture to traverse the capillary track region to a viewing region of the slide assay device; and (6) visually determining the absence or presence of the analyte in the determinable volume of environmental sample by observing the presence or absence, respectively, of significant agglutinated latex particles in the viewing region of the slide assay device.

12. A method according to claim 11 wherein the pores and interstices of the permeable membrane are within the range of from about 0.4 to 0.7 µm and the coated particles located on the first surface and entrapped in the pores and interstices of the permeable membrane are within the range of about 0.8 to 1.0 µm.

13. A method according to claim 12 wherein the permeable membrane is a glass fiber membrane.

14. A method according to claim 12 wherein the coated particles are polystyrene latex particles.

15. A method according to claim 11 wherein the analyte is atrazine.

16. A method according to claim 11 wherein the analyte is atrazine, the coated particles are polystyrene latex particles within the range of about 0.8 to 1.0 µm, the permeable membrane is a glass fiber membrane having pores and interstices in the range of from about 0.4 to 0.7 µm and the fractional volume of the eluting solvent is no greater than about 1/50 of the determinable volume of sample.

17. A method according to claim 11 wherein the eluting solvent is a solution of about 60% methanol (v/v), about 40% ethylene glycol (v/v), about 4% polyvinyl pyrrolidone (w/v) and about 2% NaCl (w/v).

18. A method according to claim 16 wherein the eluting solvent is a solution of about 60% methanol (v/v), about 40% ethylene glycol (v/v), about 4% polyvinyl pyrrolidone (w/v) and about 2% NaCl (w/v).

19. A method for concentrating an analyte present in a sample in an amount of 10 ppb or less for detecting the possible presence of said analyte in an agglutination reaction assay in an agglutination reaction slide assay device, said method comprising:

(1) providing a determinable volume of said sample;

(2) providing a permeable membrane in a liquid tight housing, said housing having an inlet port to a first surface of the membrane and an outlet port from a second, opposite surface of the membrane, said permeable membrane having pore or interstices therein and having latex particles coated with an antibody or affinity reagent to the analyte, located on the first surface and entrapped in the pores or interstices of the permeable membrane;

(3) introducing said determinable volume of sample under a pressure differential into the inlet port for travel through the permeable membrane and out the outlet port, with analyte in the sample binding to the antibody or affinity reagent coated on the particles; and (4) thereafter, employing a volume of eluting solvent which is a fractional part of the said determinable volume of sample, said eluting solvent comprising a solution of methanol, ethylene glycol, polyvinyl pyrrolidone and NaCl, eluting analyte from the coated particles out the outlet port into a container as a concentrated analyte solution having a concentration of the analyte of at least about 50 ppb.

20. A method according to claim 19 wherein the pores and interstices of the permeable membrane are within the range of from about 0.4 to 0.7 µm and the coated particles located on the first surface and entrapped in the pores and interstices of the permeable membrane are within the range of about 0.8 to 1.0 µm.

21. A method according to claim 20 wherein the permeable membrane is a glass fiber membrane.

22. A method according to claim 20 wherein the coated particles are polystyrene latex particles.

23. A method according to claim 19 wherein the sample is an environmental sample and the analyte is an organic pesticide.

24. A method according to claim 23 wherein the analyte is atrazine.

25. A method according to claim 19 wherein the sample is a biological sample and the analyte is LSD.

26. A method according to claim 19 wherein the sample is an environmental sample, the analyte is atrazine, the coated particles are polystyrene latex particles within the range of about 0.8 to 1.0 μm, the permeable membrane is a glass fiber membrane having pores and interstices in the range of from about 0.4 to 0.7 μm and the fractional volume of the eluting solvent is no greater than about 1/50 of the determinable volume of sample.

27. A method according to claim 19 wherein the eluting solvent is a solution of about 60% methanol (v/v), about 40% ethylene glycol (v/v), about 4% polyvinyl pyrrolidone (w/v) and about 2% NaCl (w/v).

28. A method according to claim 26 wherein the eluting solvent is a solution of about 60% methanol (v/v), about 40% ethylene glycol (v/v), about 4% polyvinyl pyrrolidone (w/v) and about 2% NaCl (w/v).

* * * * *